US009090870B2

(12) United States Patent
Zorn et al.

(10) Patent No.: US 9,090,870 B2
(45) Date of Patent: Jul. 28, 2015

(54) ENZYMATIC SYNTHESIS OF NOOTKATONE (75) Inventors: Holger Zorn, Wettenberg (DE); Marco Alexander Fraatz, Giessen (DE); Stephanie Johanna Luise Reimer, Hannover (DE); Meike Takenberg, Garbsen (DE); Ulrich Krings, Landesbergen (DE); Ralf Günter Berger, Hannover (DE); Stefan Marx, Roβdorf (DE)

(73) Assignee: N-ZYME BIOTEC GMBH, Darmstadt (DE)

( * ) Notice: Subject to any disclaimer, the term of this patent is extended or adjusted under 35 U.S.C. 154(b) by 716 days.

(21) Appl. No.: 13/130,980

(22) PCT Filed: Nov. 24, 2009

(86) PCT No.: PCT/EP2009/065716
§ 371 (c)(1),
(2), (4) Date: Oct. 7, 2011

(87) PCT Pub. No.: WO2010/060898
PCT Pub. Date: Jun. 3, 2010

(65) Prior Publication Data
US 2012/0045806 A1 Feb. 23, 2012

(30) Foreign Application Priority Data

Nov. 25, 2008 (EP) .................................. 08169898
Dec. 10, 2008 (EP) .................................. 08171148

(51) Int. Cl.
*C12N 9/02* (2006.01)
*C12N 15/00* (2006.01)
*C12P 7/26* (2006.01)
(52) U.S. Cl.
CPC ................. *C12N 9/0069* (2013.01); *C12P 7/26* (2013.01)

(58) Field of Classification Search
CPC .. C12N 15/1031; C12N 15/00; C12N 9/0069; C12N 15/0031
See application file for complete search history.

(56) References Cited

U.S. PATENT DOCUMENTS 6,921,847 B2 * 7/2005 Navarro Acevedo et al. 800/279

FOREIGN PATENT DOCUMENTS

WO   WO-2005/078110 A1   8/2005

OTHER PUBLICATIONS

XM_001549787.1. NCBI Reference Sequence. Feb. 26, 2008.*
Branden et al. Introduction to Protein Structure, Garland Publishing Inc., New York, p. 247, 1991.*
Fraatz et al. A novel oxygenase from Pleurotus sapidus transforms valencene to nootkatone. J. Mol. Catal., B Enzym. 61:202-207(2009).*
Furusawa Mai et al: "Highly efficient production of nootkatone, the grapefruit aroma from valencene, by biotransformation." Chemical & Pharmaceutical Bulletin, 2005, vol. 53, No. 11, pp. 1513-1514.
Database UniProt Aug. 21, 2007, "SubName: Full-Putative uncharacterized protein"; retrieved from EBI accession No. UNIPROT: A6SG40.
Database EMBL Jan. 10, 2009, "Pleurotus sapidus mRNA for valencene oxygenase (a0x1 gene)" retrieve from EBI accession No. EMBL: FM200795.
International Search Report issued in Application No. PCT/EP2009/065716, mailed Feb. 1, 2010.

* cited by examiner

*Primary Examiner* — Yong Pak
(74) *Attorney, Agent, or Firm* — Venable, LLC; Therese M. Finan; Nancy J. Axelrod (57) ABSTRACT

Polypeptide with an amino acid sequence according to SEQ ID No. 1 or a variant in which up to 10% of the amino acids have been altered by insertions, deletions or substitution.

7 Claims, 8 Drawing Sheets

◆ α-nootkatol  ▲ β-nootkatol  ─□─ (+)-nootkatone  ▲ (+)-valencene

Fxx = fraction No. xx (15 µL each), Fxx = active fractions

```
A. fumigatus    TSVTIYNRELIKRKDLRAGGEKQDQKHKVTDEAHDWAWRYAKTCVQCSDWLRHEVTVHLT   420
P. sapidus      ------------------------------------------------------------

A. fumigatus    NTHMIEEAIIVASHRQLDPDHPVMLLLYPHWQKTLALNAAARNTLVPHVIVDLIGFQASE   480
P. sapidus      ------------------------------------------------------------

┌─────Peptid 66-1─────┐
A. fumigatus    GFAFIRHAYENFDFKGRYVPTDLRQRGFPPEELDSPKFHNYAYARCINSMWHKIRSYVQD   540
P. sapidus      ------------------------|-GFPVDQLNSPK-|--------------------   11
                                        *** ;:*:***

A. fumigatus    MLALAYPGTDADHKVRNDQCIQAWSDEMRSSDGARLPSFPTISTFEELVDCVTMCIHIAS   600
P. sapidus      ------------------------------------------------------------

┌────Peptid 66-3────┐
A. fumigatus    PQHTAVNYLQNYYQSFVVNKPPCLYTEPPTSLQSLLGYTEKELVEALPMNHPREWLLASH   660
P. sapidus      --------------------------------|-YTESDLMAALPLN-|---------   24
                                                 ***.;*; ***:*

A. fumigatus    IPYLLSFKPGNKESLIVYAASKFRVYHNKPTEKDQAIAAATGKFNTALAESQEEFKRYGQ   720
P. sapidus      ------------------------------------------------------------

A. fumigatus    ATDDWETVEYEVLSPEWNAVSILI   744
P. sapidus      ------------------------
```

Fig.8

Sequence 2: cDNA-sequence

ATGCGGTACGGCTGTGCGGCGGTTGCATTATTCTACCTTACAGCAATGGGAAAGCTGCACCCTTTGGCCATCATC
CCCGACTACAAAGGCAGCATGGCCGCTTCGGTCACCATCTTCAACAAACGTACCAATCCATTAGACATATCCGTG
AATCAGGCTAACGACTGGCCATGGCGCTACGCCAAGACATGCGTCCTTTCTTCGGATTGGGCCCTCCACGAGATG
ATCATCCATCTTAACAACACCCATCTTGTGGAAGAAGCAGTCATCGTGGCGGCACAGCGCAAACTGTCCCCTTCA
CACATCGTGTTCCGGCTTTTGGAACCACATTGGGTTGTCACATTGTCCCTCAATGCACTTGCGCGCAGCGTCCTT
ATCCCCGAAGTCATCGTTCCTATAGCTGGCTTCAGTGCTCCTCATATCTTCCAATTCATCCGCGAATCATTCACC
AACTTCGACTGGAAGAGCCTCTACGTCCCAGCGGACTTGGAGTCACGTGGTTTCCCCGTCGACCAACTCAACTCG
CCGAAATTCCACAACTACGCCTATGCCAGGGATATCAACGATATGTGGACAACCTTGAAGAAGTTTGTATCGTCC
GTTCTGCAGGATGCCCAATATTACCCGGATGATGCCTCGGTAGCTGGAGATACGCAAATTCAGGCCTGGTGTGAT
GAGATGCGGTCGGGGATGGGTGCCGGATGACAAACTTCCCAGAGTCGATCACAACAGTGGACGATCTGGTCAAC
ATGGTCACAATGTGCATCCACATCGCTGCGCCTCAGCACACCGCCGTCAACTACCTTCAGCAATACTATCAGACC
TTCGTCTCCAACAAGCCATCAGCATTATTCTCGCCACTCCCGACCTCGATTGCTCAACTTCAGAAATACACCGAA
AGCGACCTGATGGCAGCTCTCCCTCTCAATGCCAAACGCCAGTGGTTACTCATGGCACAGATCCCGTATTTGCTT
TCCATGCAAGTCCAAGAAGACGAAAATATCGTGACCTATGCTGCTAATGCATCAACTGATAAAGATCCCATCATC
GCGAGCGCTGGTAGGCAGTTAGCTGCCGATTTGAAGAAACTCGCTGCGGTATTTTTGGTGAATAGCGCTCAGTTA
GATGATCAGAACACCCCATACGATGTCCTGGCACCCGAGCAACTCGCAAATGCGATTGTAATTTGA

Sequence 1: amino acid sequence

MRYGCAAVALFYLTAMGKLHPLAIIPDYKGSMAASVTIFNKRTNPLDISVNQANDWPWRYAKTCVLSSDWALHEM
IIHLNNTHLVEEAVIVAAQRKLSPSHIVFRLLEPHWVVTLSLNALARSVLIPEVIVPIAGFSAPHIPQFIRESFT
NFDWKSLYVPADLESRGFPVDQLNSPKFHNYAYARDINDMWTTLKKFVSSVLQDAQYYPDDASVAGDTQIQAWCD
EMRSGMGAGMTNFPESITTVDDLVNMVTMCIHIAAPQHTAVNYLQQYYQTFVSNKPSALFSPLPTSIAQLQKYTE
SDLMAALPLNAKRQWLLMAQIPYLLSMQVQEDENIVTYAANASTDXDPIIASAGRQLAADLKKLAAVFLVNSAQL
DDQNTPYDVLAPEQLANAIVI

SEQUENCE LISTING

```
<160> NUMBER OF SEQ ID NOS: 10

<210> SEQ ID NO 1
<211> LENGTH: 396
<212> TYPE: PRT
<213> ORGANISM: Pleurotus sapidus

<400> SEQUENCE: 1

Met Arg Tyr Gly Cys Ala Ala Val Ala Leu Phe Tyr Leu Thr Ala Met
1               5                   10                  15

Gly Lys Leu His Pro Leu Ala Ile Ile Pro Asp Tyr Lys Gly Ser Met
                20                  25                  30

Ala Ala Ser Val Thr Ile Phe Asn Lys Arg Thr Asn Pro Leu Asp Ile
            35                  40                  45

Ser Val Asn Gln Ala Asn Asp Trp Pro Trp Arg Tyr Ala Lys Thr Cys
        50                  55                  60

Val Leu Ser Ser Asp Trp Ala Leu His Glu Met Ile Ile His Leu Asn
65                  70                  75                  80

Asn Thr His Leu Val Glu Glu Ala Val Ile Val Ala Ala Gln Arg Lys
                85                  90                  95

Leu Ser Pro Ser His Ile Val Phe Arg Leu Leu Glu Pro His Trp Val
            100                 105                 110

Val Thr Leu Ser Leu Asn Ala Leu Ala Arg Ser Val Leu Ile Pro Glu
        115                 120                 125

Val Ile Val Pro Ile Ala Gly Phe Ser Ala Pro His Ile Phe Gln Phe
    130                 135                 140

Ile Arg Glu Ser Phe Thr Asn Phe Asp Trp Lys Ser Leu Tyr Val Pro
145                 150                 155                 160

Ala Asp Leu Glu Ser Arg Gly Phe Pro Val Asp Gln Leu Asn Ser Pro
                165                 170                 175

Lys Phe His Asn Tyr Ala Tyr Ala Arg Asp Ile Asn Asp Met Trp Thr
            180                 185                 190

Thr Leu Lys Lys Phe Val Ser Ser Val Leu Gln Asp Ala Gln Tyr Tyr
        195                 200                 205

Pro Asp Asp Ala Ser Val Ala Gly Asp Thr Gln Ile Gln Ala Trp Cys
    210                 215                 220

Asp Glu Met Arg Ser Gly Met Gly Ala Gly Met Thr Asn Phe Pro Glu
225                 230                 235                 240

Ser Ile Thr Thr Val Asp Asp Leu Val Asn Met Val Thr Met Cys Ile
                245                 250                 255

His Ile Ala Ala Pro Gln His Thr Ala Val Asn Tyr Leu Gln Gln Tyr
            260                 265                 270
```

```
Tyr Gln Thr Phe Val Ser Asn Lys Pro Ser Ala Leu Phe Ser Pro Leu
            275                 280                 285

Pro Thr Ser Ile Ala Gln Leu Gln Lys Tyr Thr Glu Ser Asp Leu Met
290                 295                 300

Ala Ala Leu Pro Leu Asn Ala Lys Arg Gln Trp Leu Leu Met Ala Gln
305                 310                 315                 320

Ile Pro Tyr Leu Leu Ser Met Gln Val Gln Glu Asp Glu Asn Ile Val
            325                 330                 335

Thr Tyr Ala Ala Asn Ala Ser Thr Asp Lys Asp Pro Ile Ile Ala Ser
                340                 345                 350

Ala Gly Arg Gln Leu Ala Ala Asp Leu Lys Lys Leu Ala Ala Val Phe
            355                 360                 365

Leu Val Asn Ser Ala Gln Leu Asp Asp Gln Asn Thr Pro Tyr Asp Val
            370                 375                 380

Leu Ala Pro Glu Gln Leu Ala Asn Ala Ile Val Ile
385                 390                 395
```

<210> SEQ ID NO 2
<211> LENGTH: 1191
<212> TYPE: DNA
<213> ORGANISM: Pleurotus sapidus

<400> SEQUENCE: 2

```
atgcggtacg gctgtgcggc ggttgcatta ttctacctta cagcaatggg aaagctgcac    60
cctttggcca tcatcccga ctacaaaggc agcatggccg cttcggtcac catcttcaac   120
aaacgtacca atccattaga catatccgtg aatcaggcta acgactggcc atggcgctac   180
gccaagacat gcgtcctttc ttcggattgg gccctccacg agatgatcat ccatcttaac   240
aacacccatc ttgtggaaga agcagtcatc gtggcggcac agcgcaaact gtccccttca   300
cacatcgtgt tccggctttt ggaaccacat tgggttgtca cattgtccct caatgcactt   360
gcgcgcagcg tccttatccc cgaagtcatc gttcctatag ctggcttcag tgctcctcat   420
atcttccaat tcatccgcga atcattcacc aacttcgact ggaagagcct ctacgtccca   480
gcggacttgg agtcacgtgg tttccccgtc gaccaactca actcgccgaa attccacaac   540
tacgcctatg ccagggatat caacgatatg tggacaacct tgaagaagtt tgtatcgtcc   600
gttctgcagg atgcccaata ttacccggat gatgcctcgg tagctggaga tacgcaaatt   660
caggcctggt gtgatgagat gcggtcgggg atgggtgccg ggatgacaaa cttcccagag   720
tcgatcacaa cagtggacga tctggtcaac atggtcacaa tgtgcatcca catcgctgcg   780
cctcagcaca ccgccgtcaa ctaccttcag caatactatc agaccttcgt ctccaacaag   840
ccatcagcat tattctcgcc actcccgacc tcgattgctc aacttcagaa atacaccgaa   900
agcgacctga tggcagctct ccctctcaat gccaaacgcc agtggttact catggcacag   960
atcccgtatt tgctttccat gcaagtccaa gaagacgaaa atatcgtgac ctatgctgct  1020
aatgcatcaa ctgataaaga tcccatcatc gcgagcgctg gtaggcagtt agctgccgat  1080
ttgaagaaac tcgctgcggt atttttggtg aatagcgctc agttagatga tcagaacacc  1140
ccatacgatg tcctggcacc cgagcaactc gcaaatgcga ttgtaatttg a           1191
```

<210> SEQ ID NO 3
<211> LENGTH: 11
<212> TYPE: PRT
<213> ORGANISM: Pleurotus sapidus

```
<400> SEQUENCE: 3

Gly Phe Pro Val Asp Gln Leu Asn Ser Pro Lys
1               5                   10

<210> SEQ ID NO 4
<211> LENGTH: 12
<212> TYPE: PRT
<213> ORGANISM: Pleurotus sapidus

<400> SEQUENCE: 4

Asp Leu Asn Asp Met Trp Thr Thr Leu Gly Ala Lys
1               5                   10

<210> SEQ ID NO 5
<211> LENGTH: 15
<212> TYPE: PRT
<213> ORGANISM: Pleurotus sapidus

<400> SEQUENCE: 5

Tyr Thr Glu Ser Asp Leu Met Ala Ala Leu Pro Leu Asn Ala Lys
1               5                   10                  15

<210> SEQ ID NO 6
<211> LENGTH: 17
<212> TYPE: PRT
<213> ORGANISM: Pleurotus sapidus

<400> SEQUENCE: 6

Thr Asn Pro Leu Asp Leu Ser Val Asn Gln Ala Asn Asp Trp Pro Trp
1               5                   10                  15

Arg

<210> SEQ ID NO 7
<211> LENGTH: 21
<212> TYPE: DNA
<213> ORGANISM: Artificial
<220> FEATURE:
<223> OTHER INFORMATION: Primer

<400> SEQUENCE: 7
aaacctgatg aggagctgtt t                                             21

<210> SEQ ID NO 8
<211> LENGTH: 20
<212> TYPE: DNA
<213> ORGANISM: Artificial
<220> FEATURE:
<223> OTHER INFORMATION: primer

<400> SEQUENCE: 8
acaggatacg gtgatgaatg                                               20

<210> SEQ ID NO 9
<211> LENGTH: 384
<212> TYPE: PRT
<213> ORGANISM: Aspergillus fumigatus

<400> SEQUENCE: 9

Thr Ser Val Thr Ile Tyr Asn Arg Glu Leu Ile Lys Arg Lys Asp Leu
1               5                   10                  15

Arg Ala Gly Gly Glu Lys Gln Asp Gln Lys His Lys Val Thr Asp Glu
            20                  25                  30
```

Ala His Asp Trp Ala Trp Arg Tyr Ala Lys Thr Cys Val Gln Cys Ser
             35                  40                  45

Asp Trp Leu Arg His Glu Val Thr Val His Leu Thr Asn Thr His Met
 50                  55                  60

Ile Glu Glu Ala Ile Ile Val Ala Ser His Arg Gln Leu Asp Pro Asp
 65                  70                  75                  80

His Pro Val Met Leu Leu Leu Tyr Pro His Trp Gln Lys Thr Leu Ala
                 85                  90                  95

Leu Asn Ala Ala Ala Arg Asn Thr Leu Val Pro His Val Ile Val Asp
                100                 105                 110

Leu Ile Gly Phe Gln Ala Ser Glu Gly Phe Ala Phe Ile Arg His Ala
            115                 120                 125

Tyr Glu Asn Phe Asp Phe Lys Gly Arg Tyr Val Pro Thr Asp Leu Arg
            130                 135                 140

Gln Arg Gly Phe Pro Pro Glu Glu Leu Asp Ser Pro Lys Phe His Asn
145                 150                 155                 160

Tyr Ala Tyr Ala Arg Cys Ile Asn Ser Met Trp His Lys Ile Arg Ser
                165                 170                 175

Tyr Val Gln Asp Met Leu Ala Leu Ala Tyr Pro Gly Thr Asp Ala Asp
            180                 185                 190

His Lys Val Arg Asn Asp Gln Cys Ile Gln Ala Trp Ser Asp Glu Met
            195                 200                 205

Arg Ser Ser Asp Gly Ala Arg Leu Pro Ser Phe Pro Thr Ile Ser Thr
210                 215                 220

Phe Glu Glu Leu Val Asp Cys Val Thr Met Cys Ile His Ile Ala Ser
225                 230                 235                 240

Pro Gln His Thr Ala Val Asn Tyr Leu Gln Asn Tyr Tyr Gln Ser Phe
                245                 250                 255

Val Val Asn Lys Pro Pro Cys Leu Tyr Thr Glu Pro Thr Ser Leu
                260                 265                 270

Gln Ser Leu Leu Gly Tyr Thr Glu Lys Glu Leu Val Glu Ala Leu Pro
            275                 280                 285

Met Asn His Pro Arg Glu Trp Leu Leu Ala Ser His Ile Pro Tyr Leu
            290                 295                 300

Leu Ser Phe Lys Pro Gly Asn Lys Glu Ser Leu Ile Val Tyr Ala Ala
305                 310                 315                 320

Ser Lys Phe Arg Val Tyr His Asn Lys Pro Thr Glu Lys Asp Gln Ala
                325                 330                 335

Ile Ala Ala Ala Thr Gly Lys Phe Asn Thr Ala Leu Ala Glu Ser Gln
            340                 345                 350

Glu Glu Phe Lys Arg Tyr Gly Gln Ala Thr Asp Asp Trp Glu Thr Val
            355                 360                 365

Glu Tyr Glu Val Leu Ser Pro Glu Trp Asn Ala Val Ser Ile Leu Ile
370                 375                 380

<210> SEQ ID NO 10
<211> LENGTH: 13
<212> TYPE: PRT
<213> ORGANISM: Pleurotus sapidus

<400> SEQUENCE: 10

Tyr Thr Glu Ser Asp Leu Met Ala Ala Leu Pro Leu Asn
1               5                   10

ENZYMATIC SYNTHESIS OF NOOTKATONE

This application is a National Stage Application of International Application No. PCT/EP2009/065716, filed Nov. 24, 2009, which claims priority to European Patent Application No. 08169898.7, filed Nov. 25, 2008 and European Patent Application No. 08171148.3, filed Dec. 10, 2008, the entire contents of which are hereby incorporated by reference in their entirety.

The present invention relates to processes for the oxidation of terpene hydrocarbons, and to polypeptides that can be employed therein.

While terpene hydrocarbons are often removed from essential oils as undesirable excess components, synthetic oxy-functionalized derivatives find broad application as flavors and perfumes. This disproportion together with the fact that the economically interesting terpenoids occur only in traces in plant sources is the cause of so far fifty years of history of microbial terpene biotransformation (Schrader and Berger 2001). (+)-Nootkatone has a smell reminding of *citrus* and grapefruit, a slightly bitter taste and an extremely low sensory threshold of about one microgram per liter of water (Ohloff 1994). This combination of properties has made nootkatone a bioproduct high in demand worldwide.

The first biotransformation of valencene mentioned in the literature dates back to the year 1973 (Dhavlikar and Albroscheit 1973). Valencene was transformed into (+)-nootkatone with two isolated *Enterobacter* species with a maximum yield of 12% (w/w). The biotransformation of valencene with cell cultures from grapefruit (*Citrus paradisi*) resulted in nootkatone contents of about 1 mg/l after six hours of incubation (Drawert et al., 1984). Del Rio et al. used different *Citrus* species for the biosynthesis of nootkatone and achieved the highest nootkatone yields with nine month old callus cultures from *Citrus paradisi* (1.6 µg per g of wet biomass). In 1994, the biosynthesis of nootkatone by a *Rhodococcus* strain (KSM-5706) was described (Okuda et al. 1994), but the yields were also low.

Among the novel approaches of recent years, experiments with recombinant microorganisms and with plant cell cultures or plant preparations are to be mentioned. Microsomal preparations from the root of chicory (*Cichorium intybus* L.) were characterized by a negligible formation of by-products (Bouwmeester et al. 2007; de Kraker et al. 2003), but there is no practicable way to obtain sufficient amounts of this biocatalyst in the foreseeable future. The oxy functionalization of (+)-valencene with recombinant $P450_{cam}$ enzymes from *Pseudomonas putida* with a maximum yield of 9% (w/w) was published in 2005 (Sowden et al. 2005). Conversion with recombinant $P450_{Bm-3}$ enzymes was also described, but resulted in a number of other products in addition to (+)-nootkatone.

Submerged cultures of the ascomycete *Chaetomium globosum* were also employed for the preparation of (+)-nootkatone from (+)-valencene (Kaspera et al. 2005). After three days of transformation, 8 mg/l of (+)-nootkatone was achieved, again with formation of numerous volatile and nonvolatile by-products. In addition, plant cell cultures of *Gynostemma pentaphyllum, Caragana chamlagu* and *Hibiscus cannabinus* are capable of synthesizing nootkatone from (+)-valencene (Sakamaki et al. 2005). Maximum yields of (+)-nootkatone were achieved with *Gynostemma pentaphyllum* (Cucurbitaceae), but only after 20 days of transformation (600 mg/l). Long incubation times were also necessary for submerged cultures of *Mucor* sp. and *Chlorella pyrenoidosa* (Hashimoto et al. 2003b, Hashimoto et al. 2003a; Furusawa et al. 2005).

In order to circumvent the problems associated with the use of intact cells, the use of isolated enzymes has been proposed. A Swiss flavor manufacturer describes the addition of lipoxygenase and unsaturated fatty acids to valencene (Muller et al. 1998). Laccases require synthetic cosubstrates (Hitchman et al. 2005) or a second reaction step (heating/heavy metal catalyst) (Huang et al. 2001). Good space-time yields were achieved with lyophilizates from basidiomycetes, without the relevant patent application describing a concrete process example (Müller et al. 2005).

Therefore, there is still a need for processes allowing to convert terpene hydrocarbons with high efficiency.

It is the object of the present invention to provide such a process.

This object is achieved by providing a polypeptide suitable for the oxidation of terpene hydrocarbons, and the information necessary for preparing the enzyme recombinantly.

Therefore, the invention firstly relates to a polypeptide having an amino acid sequence according to SEQ ID No. 1 or a variant thereof in which up to 10% of the amino acids are modified by insertions, deletions or substitution.

Insertion means the insertion of one amino acid; deletion means the elimination of one amino acid. In a substitution, one amino acid is replaced by another amino acid.

In addition to the 20 naturally occurring amino acids, amino acids include amino acid derivatives, such as hydroxyproline, derivatives that can be obtained by esterification of carboxylic acids or by amide formation or the like. In addition to the natural L-amino acids, D-amino acids may also be employed.

Preferably, a peptide is employed in which less than 10% of the amino acids have been modified by insertions, deletions or substitution, especially a maximum of 8%, a maximum of 5%, a maximum of 3% and more preferably a maximum of 1%.

In one embodiment, the peptides have C-terminal and/or N-terminal truncations.

A preferred embodiment of the protein is a protein encoded by SEQ ID No. 2 or by a nucleic acid hybridizing with it under stringent conditions.

The peptide according to the invention shows the properties of an enzyme, namely an oxygenase.

The enzyme is characterized biochemically and by molecular-biological methods and shows low sequence homologies with previously known oxygenases, whether from fungi or from other microorganisms.

The invention further relates to a nucleic acid coding for the polypeptide according to the invention, and a particularly preferred embodiment thereof is the sequence according to SEQ ID No. 2 or a sequence hybridizing with it under stringent conditions.

The invention further relates to a vector containing the nucleic acid according to the invention, and to a transformed organism containing the vector according to the invention.

The invention further relates to a process for the oxidation of terpene hydrocarbons, comprising the step of contacting terpene hydrocarbons with a polypeptide according to claim 1 or an enzyme preparation containing the polypeptide according to claim 1.

Thus, the material employed may be a purified enzyme from natural sources or from recombinant production or an enzyme preparation. The latter can be obtained from the mycelium of a basidiomycete by physical, chemical or enzymatic digestion.

Preferably, such a digestion is effected by dispersion, ball milling or high-pressure homogenization.

Freeze drying or lyophilization is not a digestion; therefore, lyophilization alone does not yield the desired result. Therefore, lyophilization alone without further homogenization steps is excluded.

In particular, basidiomycetes from the Pleurotaceae family, especially *Pleurotus sapidus*, are suitable as basidiomycetes.

More preferably, the process according to the invention can be employed for obtaining nootkatone from valencene. However, any other terpene hydrocarbons may also be employed.

The invention is further illustrated by the following Examples.

FIG. 8 shows the cDNA and amino acid sequence of the polypeptide according to the invention from *P. sapidus*, the start and stop codons being marked in boldface.

EXAMPLES

Example 1

Microorganism and Culturing

*Pleurotus sapidus* (DSMZ 8266) was obtained from the Deutsche Sammlung für Mikroorganismen and Zellkulturen (DSMZ), Braunschweig, Germany.

a) Nutrient Solutions

The individual components (Table 1) were dissolved in distilled water and adjusted to pH 6.0 with 0.5 M aqueous sodium hydroxide.

TABLE 1

|  | Glc c [g L$^{-1}$] | Molasses c [g L$^{-1}$] | Asn c [g L$^{-1}$] | NH$_4$NO$_3$ c [g L$^{-1}$] | KH$_2$PO$_4$ c [g L$^{-1}$] | MgSO$_4$ c [g L$^{-1}$] | Yeast extract c [g L$^{-1}$] | SE-Lsg c [g L$^{-1}$] |
|---|---|---|---|---|---|---|---|---|
| SNL-H* | 30 | 0 | 4.5 | 0.0 | 1.5 | 0.5 | 3.0 | 1.0 |
| NLMA | 0 | 81 | 0 | 2.4 | 1.5 | 0.5 | 3.0 | 1.0 |

Composition of the nutrient solutions; Glc = D-(+)-glucose monohydrate, Asn = L-asparagine monohydrate, SE-Lsg = trace element solution (Table 2) = concentration,
*= modified according to Sprecher 1959

TABLE 2

Composition of the trace element solution

| Substance | Concentration [g L$^{-1}$] |
|---|---|
| FeCl$_3$•6 H$_2$O | 0.080 |
| ZnSO$_4$•7 H$_2$O | 0.090 |
| MnSO$_4$•H$_2$O | 0.030 |
| CuSO$_4$•5 H$_2$O | 0.005 |
| EDTA | 0.400 | b) Stock Culturing

Of *Pleurotus sapidus*, stock cultures were started on agar plates with SNL-H-agar medium. Thus, one agar plate each was inoculated with an about 1 cm$^2$ sized agar piece overgrown with mycelium, sealed with Parafilm® and cultured in an incubator at 24° C. (Taubert et al., 2000). After the plates were half overgrown with mycelium, the culture was stored at 4° C. These stock cultures were passaged by the same method at least every 6 months.

c) Preliminary Cultures

An agar piece overgrown with mycelium (about 1 cm$^2$) from the stock culture was transferred into an Erlenmeyer flask (500 ml) with 200 ml of SNL-H medium by means of a sterile spatula, homogenized (Ultra-Turrax homogenizer, TP 18/10, IKA, Staufen, Germany, about 20 s at a low rotational speed) and incubated at 24° C. and with 150 rpm for 4 days.

d) Cultivating Biomass

In a stirred tank reactor, 2.3 l of NLMA medium was inoculated with 230 ml of homogenized preliminary culture. After 4 days, the content of the stirred tank reactor was harvested. For this purpose, it was filtered through a cotton cloth. The mushroom mycelium obtained was washed twice with 400 ml each of distilled water (m/v) and used for further experiments. The cultivation was performed under a clean bench, and the equipment and solutions employed were previously autoclaved at 121° C. for 20 min.

Example 2

Cell Lysis a) Homogenization of Wet Biomass

Three grams of wet biomass was admixed with 7 ml of 50 mM Tris-HCl, pH 7.5, and subsequently treated at 15,600 rpm for 5 min on ice using an Ultra-Turrax homogenizer (TP 18/10, IKA). Subsequently, the digested mushroom mycelium was diluted to 16.7% (v/v) with the same buffer and used for the transformation of (+)-valencene.

b) Homogenization of Wet Biomass—Upscaling

Fifty grams of wet biomass was admixed with 50 ml of 50 mM Tris-HCl, pH 7.5, and subsequently treated at 20,000 rpm for 15 min on ice using an Ultra-Turrax homogenizer (TP 18/10, IKA). Subsequently, the digested mushroom mycelium was diluted to 25% (v/v) with the same buffer and used for the transformation of (+)-valencene.

c) Homogenization of Wet Biomass Under High Pressure

Suspensions of mushroom mycelium in fully desalted water were digested by means of high-pressure homogenization (LAB 60/60 TBS, Gaulin APV, Switzerland). Cooled mycelium was digested by 1 to 3 runs (150/30 bar and 300/60 bar) and directly employed for the biotransformation reaction. Alternatively, valencene was introduced and homogenized directly during the cell lysis.

d) Production of Lyophilizates

Up to 100 g of wet biomass was weighed into a glass Petri dish, covered with aluminum foil and deep frozen at −20° C. The lyophilization was performed for 3 to 7 days (VaCo 2, Zirbus Technology, Bad Grund, Germany). The tray temperature was −20° C., and the temperature of the cooling coil was −45° C. The lyophilizate obtained was weighed, comminuted with a glass rod, transferred into sterile Falcon™ tubes and stored at −70° C. until use.

Example 3

Biotransformation of Valencene a) Transformation with Digested Biomass

Figure 1:
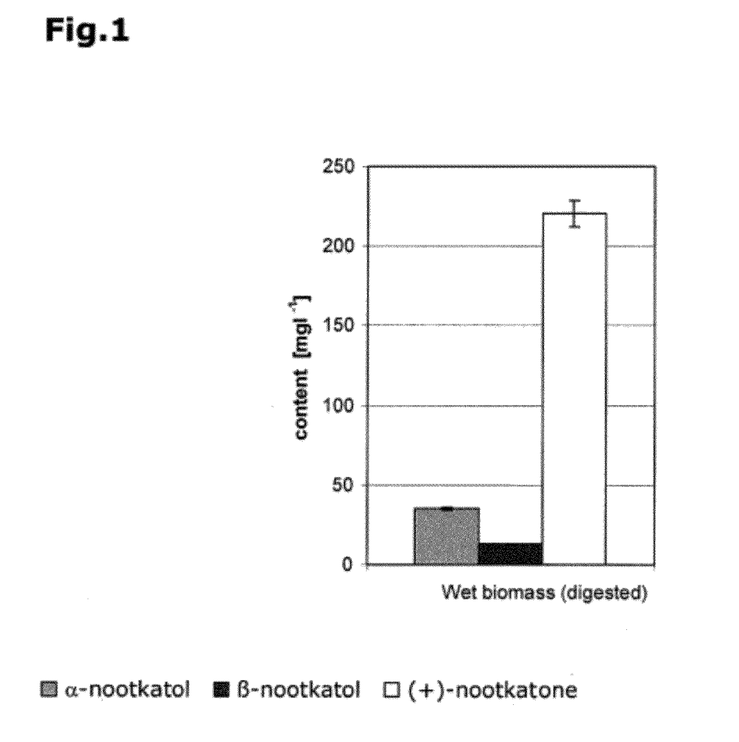
FIG. 1 shows the product yields after transformation of (+)-valencene with digested wet biomass; transformation of 2 μl of (+)-valencene with wet biomass (digested) in 1.5 ml of 50 mM Tris-HCl, pH 7.5, for 16 hours.

The transformation was performed in screw-cap vials (4 ml) in horizontal position at 300 rpm and at 24° C. Wet biomass of *Pleurotus sapidus* (1.5 ml) was treated with an Ultra-Turrax homogenizer and used for the transformation of 2 µl of (+)-valencene (Döhler, 70%). After completion of the transformation, an extraction was performed. The determined content of (+)-nootkatone was 221 mg/l (FIG. 1).

b) Fed-Batch Transformation of Valencene

Figure 2:
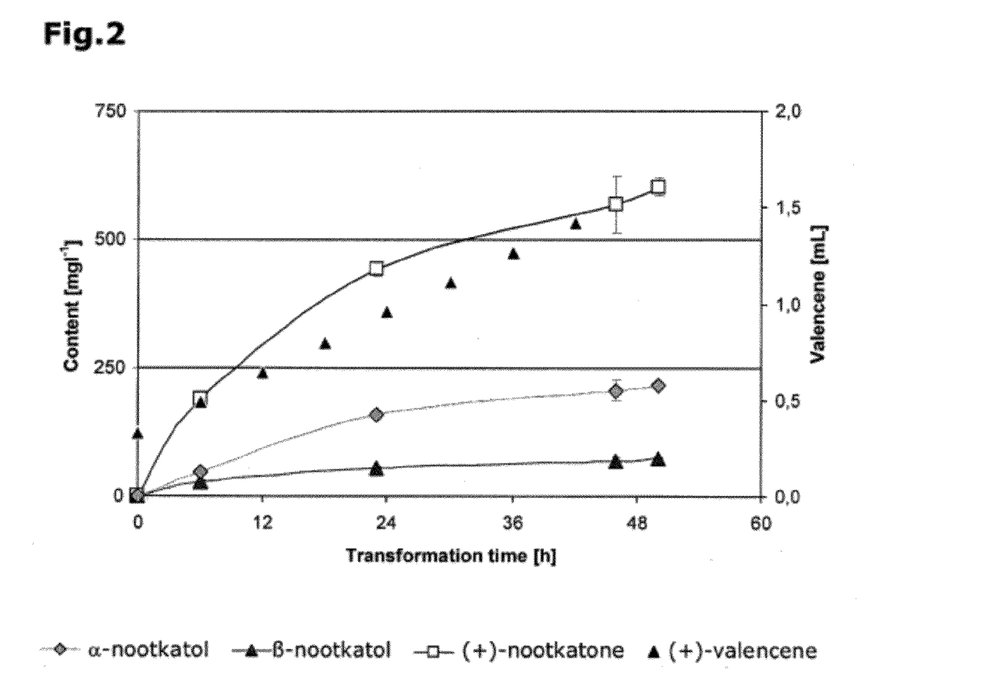
FIG. 2 shows the product yields after fed-batch transformation of (+)-valencene with digested wet biomass in 100 ml of 50 mM Tris-HCl, pH 7.5, for 50 hours.
Figure 4:
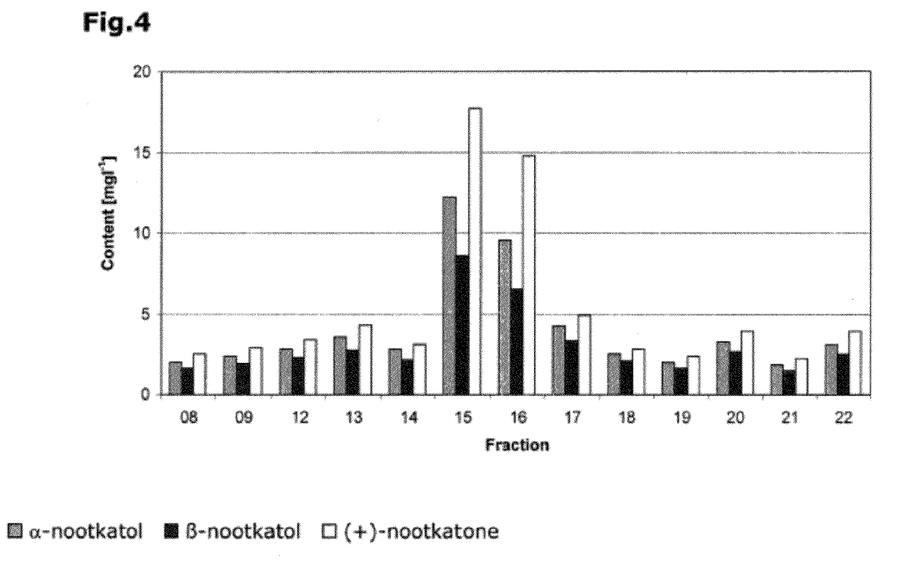
FIG. 4 shows the product yields after transformation with FPLC fractions of the 3rd purification stage; transformation of 1 μl of (+)-valencene in a volume of 1.5 ml for 20 hours; buffer: 20 mM Tris-HCl, pH 7.5.

The transformation was performed in glass bottles (500 ml) on a magnetic stirrer (Variomag Poly 15, Thermo Fisher Scientific, Waltham, Mass., USA) at 900 rpm and at room temperature. The transformation was started by adding 333 µl of (+)-valencene (Döbler, ≥70%) to 100 ml of cell suspension (homogenized). After 6, 12, 18, 24, 30, 36 and 42 hours, doses of 156 µl each of (+)-valencene were added. After 6, 23, 46 and 50 hours, samples of 2×1.5 ml each were withdrawn and extracted. After 50 hours of transformation, the content of (+)-nootkatone was 603 mg/l (FIG. 2). In total, 893 mg/l of α-, β-nootkatol and (+)-nootkatone was formed.

c) Transformation with Purified Enzyme Solution 0.5 ml of purified protein fraction (fractions 08, 09 and 12 to 22) was mixed with 1.0 ml of 20 mM Tris-HCl, pH 7.5. Subsequently, the transformation was started by adding 1 µl of (+)-valencene (Fluka, ≥90%). The transformation was performed in screw-cap vials (4 ml) in horizontal position at 150 rpm and at 24° C. After completion of the transformation, an extraction was performed. Significant contents of the transformation products α-, β-nootkatol and (+)-nootkatone were detected after reaction with fractions 15 and 16 (FIG. 4).

d) Capillary Gas Chromatography (GC)—Microextraction after Transformation

The microextraction was performed directly in the screw-cap vial used for transformation. The mixture was admixed with internal standard (67 mg/l and 200 mg/l thymol) and 2 ml of pentane, vortexed for 10 s, and shaken in horizontal position at 150 rpm for 10 min. After centrifugation (10 min, 3313×g, 4° C.), the organic phase was dried over sodium sulfate and examined by gas chromatography.

e) Capillary Gas Chromatography (HRGC)

The quantification of α-, β-nootkatol and (+)-nootkatone by means of FID was effected with a cold injection system and a polar column.

TABLE 3

| GC-FID (CIS) with polar column | |
|---|---|
| Gas chromatograph | Hewlett Packard HP 6890 Series GC Systems |
| Injector | Gerstel KAS 4 + Gerstel Controller 505 |
| CIS parameters | splitless (0.5 min); 60° C. (0 min), 12° C. s$^{-1}$-240° C. (3 min) |
| CIS liner | Gerstel baffled glass liner |
| Column | Varian WCOT Fused Silica CP Wax 52CB, 30 m × 0.25 mm ID, 0.25 mm film thickness |
| Detector | FID, 250° C., gases: H$_2$: 40 ml min$^{-1}$, air: 450 ml min$^{-1}$, N$_2$: 45 ml min$^{-1}$ |
| Carrier gas | H$_2$, pre-pressure: 58.4 kPa, flow rate: 1.5 ml min$^{-1}$ (constant) |
| Data acquisition | Hewlett Packard HP GC ChemStation, Version Rev. A.0504 [273] |
| Temperature program | 40° C. (2 min), 5° C. min$^{-1}$-150° C. (0 min), 3° C. min$^{-1}$-222° C. (0 min), 10° C. min$^{-1}$-240° C. (10 min) |
| Autosampler | Hewlett Packard HP 6890 Series Injector (Enhanced Parameters) |

Example 4

Enzyme Purification

Fast Protein Liquid Chromatography (FPLC)

For separating impurities, the sample was centrifuged (10 min, 13,000 rpm, 16,060×g, 4° C.), and the supernatant was injected into the FPLC (Table 4). If necessary, the sample was additionally subjected to membrane filtration (0.45 µm pore size, 25 mm, PET, Carl Roth GmbH).

a) Three-Stage Purification by Means of FPLC

Figure 3:
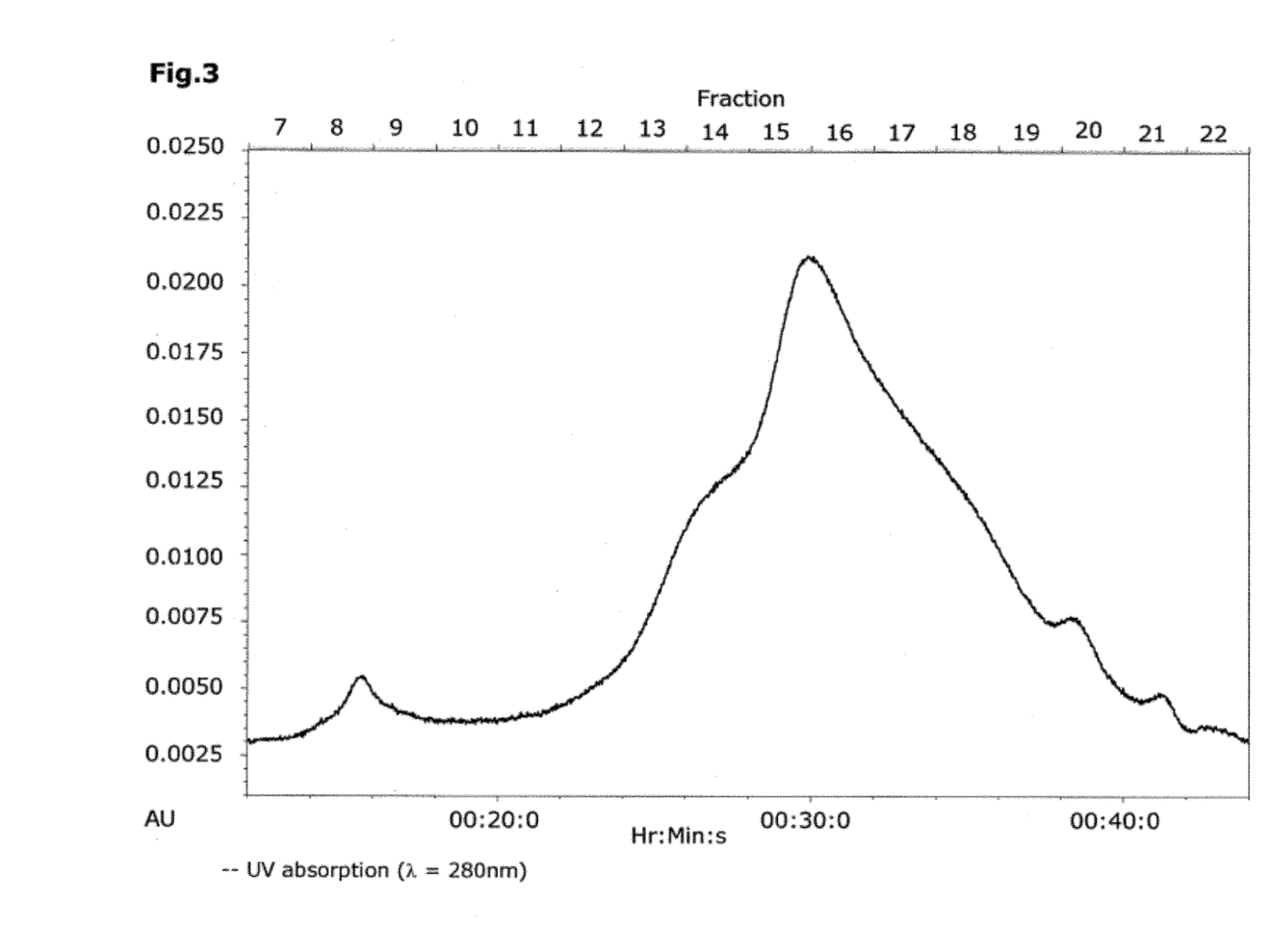
FIG. 3 shows a part of an FPLC chromatogram of the third stage of the 3-stage purification of separated supernatant on a Superdex-200 column; running buffer: 200 mM Tris-HCl, pH 7.5, flow rate: 0.5 ml/min, sample volume: 2004 fraction size: 1.0 ml.

Four times 5 ml of separated supernatant from *Pleurotus sapidus* was respectively injected into the FPLC and separated by means of the weak anion exchanger DEAE FF (see Table 5). Fractions 05 to 24 of the four FPLC runs were combined (purification stage 1, DEAE pool), rebuffered with 20 mM sodium citrate, pH 3.0 (Centricon Plus-70, exclusion size 10 kDa), and concentrated to 2.5 ml. Precipitated proteins were removed by centrifugation. 2.0 ml of the rebuffered DEAE pool was again injected into the FPLC and separated by means of the strong cation exchanger SP Sepharose FF (see Table 6). Fractions 07 to 11 were combined (purification stage 2, SP FF pool), rebuffered with 200 mM Tris-HCl, pH 7.5 (Amicon Ultra-15, exclusion size 10 kDa), and concentrated to 300 µl. Two hundred microliters of the rebuffered SP FF pool was injected into the FPLC and separated by gel filtration on a Superdex 200 column (Table 7) (purification stage 3). After calibration of the column employed, the peak maximum (30 min, FIG. 3) corresponded to a molecular weight of 54 kDa.

Figure 5:
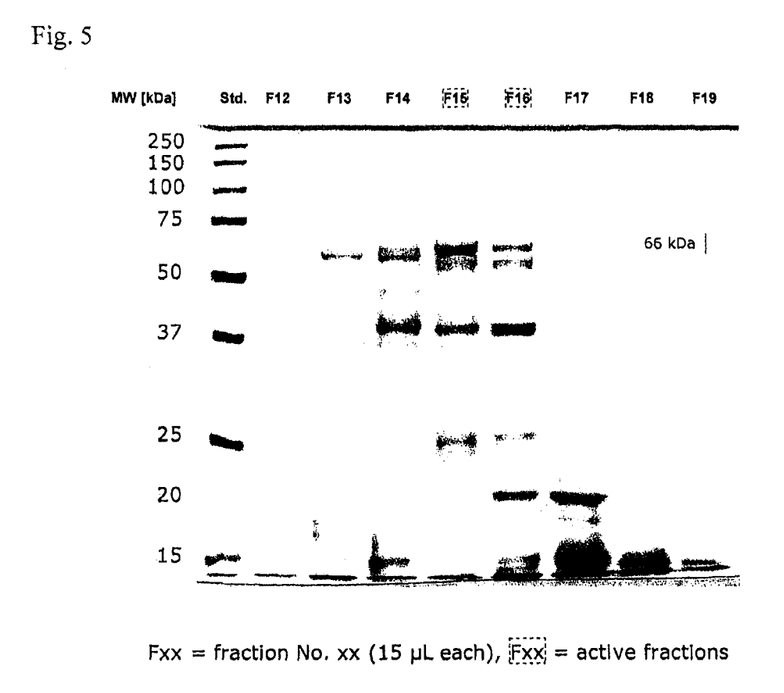
FIG. 5 shows a gel (12%) of SDS-PAGE after 3 stages of protein purification by means of FPLC with subsequent silver staining; MW=molecular weight, Std.=standard (1 μl).
Figures 6A, 6B:
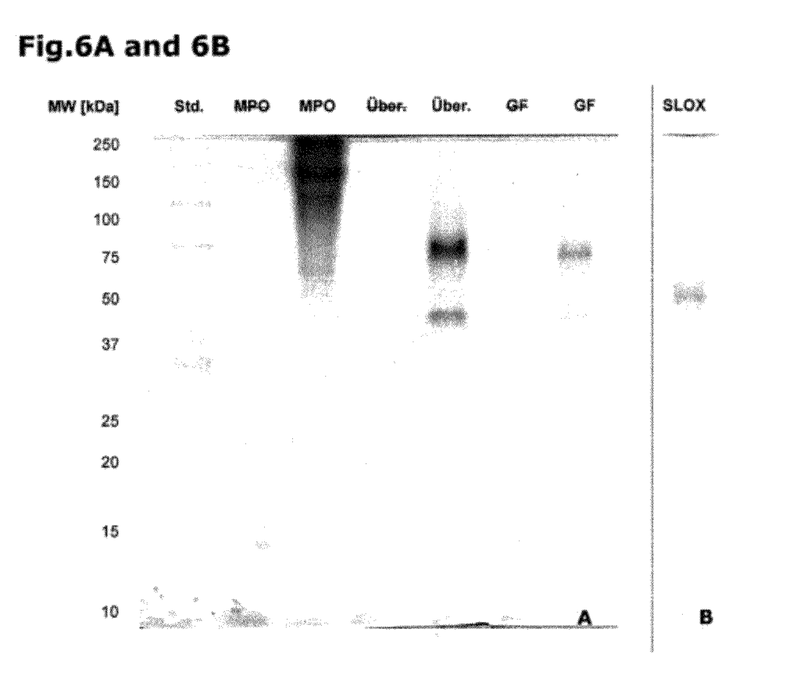
FIG. 6A shows a gel (12%) of SDS-PAGE after 3 stages of protein purification by means of FPLC with specific staining for heme enzymes/metalloenzymes (3,3',5,5'-tetramethylbenzidine); MW=molecular weight of the standard, Std.=standard (4 μl), MPO=horse radish peroxidase (15 μl, 345 mU), Über.=separated supernatant (15 μl), GF=combined active fractions from the 3rd purification stage (gel filtration, 15 μl), =the corresponding sample heated at 95° C. for 5 min before SDS-PAGE.
FIG. 6B shows a gel (12%) of SDS-PAGE with subsequent staining for heme enzymes/metalloenzymes; SLOX=lipoxygenase from soybeans (20 μl, 85 mU).

For the SDS analyses, fractions 12 to 19 were rebuffered with E-Pure water and concentrated to 80 µl (FIG. 5). These concentrates were employed for denaturing SDS-PAGE with subsequent silver staining, for non-denaturing SDS-PAGE with subsequent specific staining for heme enzymes/metalloenzymes (FIG. 6), and for the sequencing of selected protein bands after denaturing SDS-PAGE and subsequent Coomassie staining.

TABLE 4

FPLC with UV detector

| | |
|---|---|
| FPLC system | Biologic Duo Flow Chromatography System (Bio-Rad) with Biologic fraction collector Model 2128 (Bio-Rad) |
| Data acquisition | Biologic Duo Flow Workstation (Bio-Rad), Version 3.00 |
| Detection wavelength | 280 nm |

Ion-Exchange Chromatography (IEX)

TABLE 5

Enzyme purification by DEAE, step gradient

| | |
|---|---|
| Column | HiPrep 16/10 DEAE FF (Amersham Pharmacia Biotech) |
| Column volume (CV) | 20 ml |
| Starting buffer (A) | 20 mM TRIS-HCl, pH 7.5 |
| Elution buffer (B) | 20 mM TRIS-HCl + 0.2M NaCl, pH 7.5 |
| Washing buffer (C) | 20 mM TRIS-HCl + 2.0M NaCl, pH 7.5 |
| Sample loop | 5.0 ml |
| Flow rate | 5.0 ml min$^{-1}$ |
| Elution program | 2 CV 100% buffer A<br>sample injection: 2 x sample volume (buffer A)<br>7 CV of 100% buffer A<br>6 CV of 35% buffer B<br>5 CV of 100% buffer B<br>4 CV of 100% buffer C<br>5 CV of 100% buffer A |
| Fraction volume | 2.0 ml |

TABLE 6

Enzyme purification by means of SP FF

| | |
|---|---|
| Column | HiTrap SP Sepharose FF (Amersham Pharmacia Biotech) |
| Column volume (CV) | 1 ml |
| Starting buffer (A) | 20 mM sodium citrate, pH 3.0 |
| Elution buffer (B) | 20 mM sodium citrate + 1.0M NaCl, pH 3.0 |
| Sample loop | 2.0 ml or 5.0 ml |
| Flow rate | 1.0 ml min$^{-1}$ |
| Elution program | 5 CV of 100% buffer A<br>sample injection: 2 x sample volume (buffer A)<br>10 CV of 100% buffer A<br>linear gradient of 100% buffer A (0% buffer B) to 0% buffer A (100% buffer B) over 15 CV<br>5 CV of 100% buffer B<br>10 CV of 100% buffer A |
| Fraction volume | 2.0 ml |

TABLE 7

Enzyme purification by means of Superdex 200

| | |
|---|---|
| Column | Superdex 200 10/300 GL (Amersham Pharmacia Biotech) |
| Bed volume | about 24 ml |
| Separation range | 10-600 kDa |
| Sample loop | 200 ml |
| Flow rate | 0.5 ml min$^{-1}$ |
| Running buffer | 200 mM TRIS-HCl, pH 7.5 |
| Elution program | sample injection: 2 x sample volume (running buffer)<br>30 ml of 100% running buffer |
| Fraction size | 1.0 ml |

The calibration of the gel filtration column was performed using standard proteins of two gel filtration calibration kits (High Molecular Weight and Low Molecular Weight, Amersham Pharmacia Biotech) according to the manufacturer's instructions.

b) SDS-PAGE Under Denaturing Conditions

The proteins were separated in 12% separation gels (modified according to Laemmli, 1970) and visualized by Coomassie staining or silver staining (Blum et al., 1987). Both methods are known to the skilled person.

c) SDS-PAGE Under Non-Denaturing Conditions

The SDS-PAGE under non-denaturing conditions was effected by analogy with item 4b, but the composition of the loading buffer (Table 8) was modified.

TABLE 8

Composition of the loading buffer

| | |
|---|---|
| TRIS-HCl, pH 6.8 | 0.1M |
| SDS | 20 g l$^{-1}$ |
| Bromophenol blue | 2 g l$^{-1}$ |
| Glycerol | 200 g l$^{-1}$ |
| The buffer was stored in aliquots at −20° C. | | d) Staining for Heme Enzymes and Metalloenzymes (Heme Staining)

Heme staining (modified according to Thomas et al. 1976 and Henne et al. 2001) was performed only after SDS-PAGE under non-denaturing conditions. For heme staining, the following solutions were used (Table 9):

TABLE 9

Composition of the solutions for heme staining

| | |
|---|---|
| Solution I | 6.3 mM methanolic TMBZ solution |
| Solution II | 0.25M sodium acetate buffer, pH 5.0 |
| Solution III (staining solution) | Solution I/Solution II (3/7 v/v) |
| Solution IV (storing solution) | Solution II/isopropanol (7/3 v/v) |

Solutions I and III were respectively prepared shortly before use.

SDS gels were incubated in solution III in the dark for 45 min to 1 hour, followed by adding $H_2O_2$ (30%) to a final concentration of 30 mM and incubating for 1 min. The gels were washed three times in E-Pure water for 20 s each. Separated lyophilizate from *Pleurotus sapidus* was compared with the enzyme sample purified over three chromatographic stages (see Example 3, purification over three chromatographic stages (IEX, IEX, GF)). The heme-containing enzyme horseradish peroxidase and a lipoxygenase from soybean served as positive controls (FIG. 6B). Due to the specific staining, two proteins were identified as metalloenzymes, which could also be detected after the chromatographic purification over three stages. Heating of the samples before application resulted in a loss of activity.

Example 5

Peptide Sequences

By analogy with Example 4a, a three-stage chromatographic purification of the separated supernatant of *Pleurotus sapidus* was performed. After the protein purification, incubation of (+)-valencene by means of gas chromatography was used to check whether the purified fractions had activity. The active fractions 15 and 16 of the final gel filtration were separated on an SDS gel under denaturing conditions and stained with Coomassie® R (cf. analogous SDS-PAGE with silver staining in FIG. 5). The band responsible for the intended transformation activity with a calculated molecular weight of 66 kDa was cut out of the gel and, after trypsin digestion, subjected to de novo sequencing by means of "electrospray tandem mass spectrometry" (ESI-MS-MS) (Table 10).

TABLE 10

Detected peptide sequences (one-letter code) after ESI-MS-MS analysis of the enzymes purified over 3 stages; MW = molecular weight by SDS-PAGE, boldface = reliable identification

| MW [kDa] | | 66 |
|---|---|---|
| Peptide sequences | GFPVDQLNSPK | (66-1) |
| | DLNDMWTTLGAK | (66-2) |
| | YTESDLMAALPLNAK | (66-3) |
| | TNPLDLSVNQANDWPWR | (66-4) |

Figure 7:
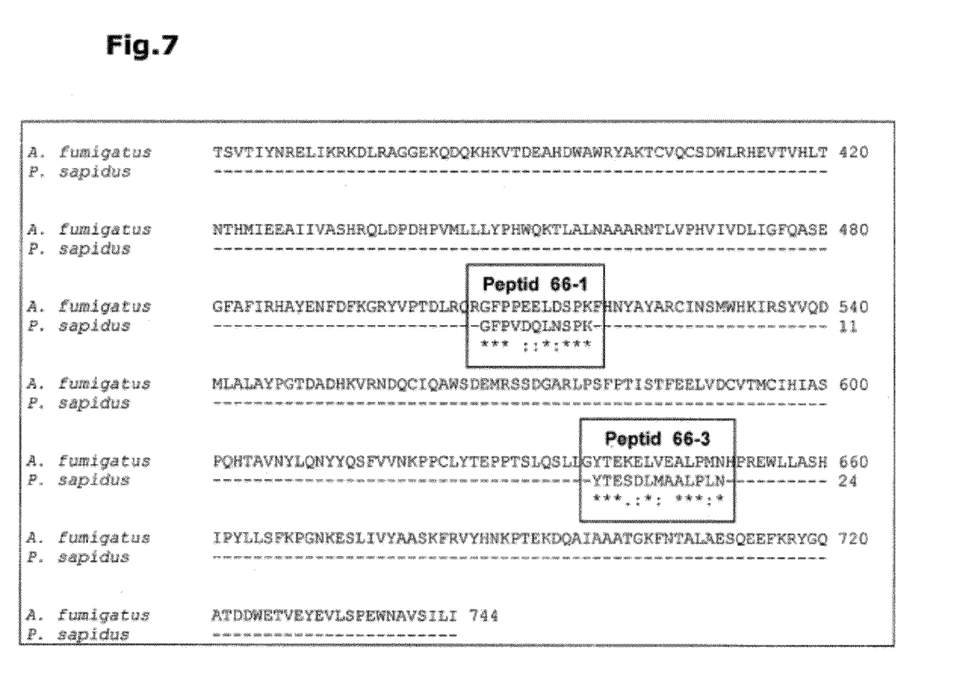
FIG. 7 shows the alignment of the peptide sequences 66-1 and 66-3 from *P. sapidus* with the sequence of a lipoxygenase from *A. fumigatus* (XP_746844.1) by means of ClustalW (Thompson et al. 1994). The sequence of the *A. fumigatus* protein is SEQ ID No: 9. The sequences of the boxed peptides #66-1 and #66-3 of *P. sapidus* are SEQ ID No. 3 and SEQ ID No. 5, respectively.

Homology comparisons were performed by database searches with NCBI Blast using blastp (Schäffer et al. 2001), and hits were found with various lipoxygenases from ascomycetes. From a comparison of peptide sequences 66-1 and 66-3 with the sequence of a lipoxygenase from *Aspergillus fumigatus* (XP_746844.1; FIG. 7), degenerate primers were derived and employed in PCR screening (Example 6, molecular characterization, cDNA synthesis and PCR screening).

Example 6

Molecular Characterization a) cDNA Synthesis and PCR Screening

For the cloning of the oxygenase-encoding cDNA sequences, cDNA from *P. sapidus* was synthesized and screened by polymerase chain reaction. The mycelium of *P. sapidus* was harvested on the 4th day of culture. For isolating the total RNA, the RNeasy Plant Mini Kit (Qiagen, Hilden, Germany) was used according to the manufacturer's instructions. The quality of the isolated RNA was checked by means of denaturing formaldehyde-agarose gel electrophoresis and staining with ethidium bromide. For the synthesis of the cDNA, the SMART™ PCR cDNA Synthesis Kit (Clontech-Takara Bio Europe, Saint-Germain-en-Laye, France) was employed according to the manufacturer's instructions. The first strand was synthesized by means of SuperScript™ II RNase H⁻ (Invitrogen, Karlsruhe, Germany). PCR primers were produced by Eurofins MWG Operon (Ebersberg, Germany). For the PCR, about 20 ng of cDNA was used as a template in 50 µl volumes with 1× CoralLoad Puffer (Qiagen), 0.2 mM dNTPs, 0.4 µM primers and 1.25 U of HotStarTaq DNA Polymerase (Qiagen). The amplification was performed with a PCR Mastercycler personal (Eppendorf, Hamburg, Germany). The following primers were used for the total sequence of the cDNA: forward (5'>AAA CCT GAT GAG GAG CTG TTT<3'); reverse (5'>ACA GGA TAC GGT GAT GAA TG<3').

b) Cloning and Sequencing of PCR Products

The PCR products were cloned into the vector pCR®2.1 by means of the TA Cloning Kit (Invitrogen). The sequencing was effected with M13 reverse and forward primers, and performed by MWG Operon. The expected fragment size in PCR screening when using the degenerate primers against each other was about 429 bp (corresponding to 143 amino acids). The corresponding band was isolated from the agarose gel, provisionally cloned into the vector pCR2.1-TOPO, and subsequently sequenced. The sequence obtained was again subjected to homology comparisons and identified as a fragment of an oxygenase.

By primer walking, the coding sequence of the cDNA having a length of 1191 bp or 396 amino acids was detected (FIG. 8). The translated protein sequence showed a homology of about 50% with an oxygenase from the basidiomycete *Laccaria* bicolor (detected with blastp, Schäffer et al. 2001).

REFERENCES

Blum, H.; Beier, H.; Gross, H. J. (1987) Improved silver staining of plant proteins, RNA and DNA in polyacrylamide gels, *Electrophoresis* 8, 93-99.

Bouwmeester, H. J.; Kraker, J.-W. de; Schurink, M.; Bino, R. J.; Groot, A. de; Franssen, M. C. R. (2007) Plant Enzymes for Bioconversion, U.S. Pat. No. 7,214,507 B2.

Dhavlikar, R. S.; Albroscheit, G. (1973) Mikrobiologische Umsetzung von Terpenen: Valencen, *Dragoco Rep* 12, 251-258.

Drawert, F.; Berger, R. G.; Godelmann, R. (1984) Regioselective biotransformation of valencene in cell suspension cultures of *Citrus* sp., *Plant Cell Rep* 3, 37-40.

Furusawa, M.; Hashimoto, T.; Noma, Y.; Asakawa, Y. (2005) Highly efficient production of nootkatone, the grapefruit aroma from valencene, by biotransformation, *Chem Pharm Bull* (Tokyo) 53, 1513-1514.

Hashimoto, T.; Asakawa, Y.; Noma, Y.; Murakimi, C.; Tanaka, M.; Kanisawa, T.; Emura, M. (2003a) Patent JP 2001-267548 20010904.

Hashimoto, T.; Asakawa, Y.; Noma, Y.; Murakimi, C.; Tanaka, M.; Kanisawa, T.; Emura, M. (2003b) Patent JP 2002-51668 20020227.

Henne, K. R.; Kunze, K. L.; Zheng, Y.-M.; Christmas, P.; Soberman, R. J.; Rettie, A. E. (2001) Covalent Linkage of Prosthetic Heme to CYP4 Family P450 Enzymes, *Biochemistry* 40, 12925-12931.

Hitchman, T.; Robertson, D. E.; Hiraiwa, M.; Phillips, Y.; Gray, K. A. (2005) Laccases, nucleic acids encoding them and methods for making and using them, Patent WO/2005/021714.

Huang, R.; Christenson, P. A.; Labuda, I. M. (2001) Process for the preparation of nootkatone by laccase catalysis, U.S. Pat. No. 6,200,786.

Kaspera, R.; Krings, U.; Nanzad, T.; Berger, R. G. (2005) Bioconversion of (+)-valencene in submerged cultures of the ascomycete *Chaetomium globosum*, *Appl Microbiol Biotechnol* 67, 477-483.

Kraker, J.-W. de; Schurink, M.; Franssen, M. C. R.; König, W. A.; Groot, A. de; Bouwmeester, H. J. (2003) Hydroxylation of sesquiterpenes by enzymes from chicory (*Cichorium intybus* L.) roots, *Tetrahedron* 59, 409-418.

Muller, B.; Dean, C.; Schmidt, C.; Kuhn, J.-C. (1998) Process for the Preparation of Nootkatone, U.S. Pat. No. 5,847,226.

Müller, M.; Dirlam, K.; Henning, H.; Berger, R. G.; Krings, U.; Kaspera, R. (2005) Verfahren zur Herstellung von aromaaktiven Terpenen, Patent DE 10 2004 006 825 A1.

Ohloff, G. (1994) Scent and fragrances: The fascination of odors and their chemical perspectives. Berlin, Springer.

Okuda, M.; Sonohara, H.; Takigawa, H.; Tajima, K.; Ito, S. (1994) Nootkatone manufacture with *Rhodococcus* from valencen, Patent JP 06303967A.

Rio, J. A. del; Ortuño, A.; Puig, D. G.; Iborra, J. L.; Sabater, F. (1991) Accumulation of the sesquiterpenes nootkatone and valencene by callus cultures of *Citrus paradisi, Citrus limonia* and *Citrus aurantium*, *Plant Cell Rep* 10, 410-413.

Sakamaki, H.; Itoh, K.-i.; Taniai, T.; Kitanaka, S.; Takagi, Y.; Chai, W.; Horiuchi, C. A. (2005) Biotransformation of valencene by cultured cells of *Gynostemma pentaphyllum*, *J Mol Catal B-Enzym* 32, 103-106.

Schäffer, A. A.; Aravind, L.; Madden, T. L.; Shavirin, S.; Spouge, J. L.; Wolf, Y. I.; Koonin, E. V.; Altschul, S. F. (2001) Improving the accuracy of PSI-BLAST protein database searches with composition-based statistics and other refinements, *Nucleic Acids Res* 29, 2994-3005.

Schrader, J.; Berger, R. G. (2001) Biotechnological production of terpenoid flavor and fragrance compounds, In: Rehm, H.-J.; Reed, G. (Hg.) Biotechnology. Special processes, 10. Weinheim, Wiley-VCH, 374-422.

Sowden, R. J.; Yasmin, S.; Rees, N. H.; Bell, S. G.; Wong, L.-L. (2005) Biotransformation of the sesquiterpene (+)-valencene by cytochrome $P450_{cam}$ and $P450_{Bm-3}$, *Org Biomol Chem* 3, 57-64.

Sprecher, E. (1959) Über die Guttation bei Pilzen, *Planta* 53, 565-574.

Taubert, J.; Krings, U.; Berger, R. G. (2000) A comparative study on the disintegration of filamentous fungi, *Journal of Microbiological Methods* 42, 225-232.

Thomas, P. E.; Ryan, D.; Levin, W. (1976) An improved staining procedure for the detection of the peroxidase activity of cytochrome P-450 on sodium dodecyl sulfate polyacrylamide gels, *Anal Biochem* 75, 168-176.

Thompson, J. D.; Higgins, D. G.; Gibson, T. J. (1994) CLUSTAL W: improving the sensitivity of progressive multiple sequence alignment through sequence weighting, position-specific gap penalties and weight matrix choice, *Nucleic Acids Res* 22, 4673-4680.

The invention claimed is:

1. A purified polypeptide which is a variant of a polypeptide comprising the amino acid sequence of SEQ ID NO:1,
   a. wherein 1 to 10% of the amino acids of SEQ ID NO:1 in the variant are modified by insertions, deletions or substitutions,
   b. wherein the variant can oxidize terpene hydrocarbons, and
   c. wherein the variant does not comprise the full-length sequence of SEQ ID NO:1.

2. A process for the oxidation of terpene hydrocarbons, comprising the step of
   contacting terpene hydrocarbons with a polypeptide according to claim 1 or an enzyme preparation containing the polypeptide according to claim 1.

3. The process according to claim 2, wherein said enzyme preparation has been obtained from the mycelium of a badidiomycete by physical, chemical or enzymatic digestion.

4. The process according to claim 3, wherein digestion is effected by dispersion, ball milling or high-pressure homogenization.

5. The process according to claim 3, wherein said basidiomycetes are from the Pleurotaceae family.

6. The process according to claim 2, wherein said terpene hydrocarbon is valencene, and nootkatone is obtained.

7. The process according to claim 5, wherein said basidiomycetes are from *Pleurotus sapidus*.

* * * * *